(12) United States Patent
Satou et al.

(10) Patent No.: US 6,955,680 B2
(45) Date of Patent: Oct. 18, 2005

(54) COUPLING VIBRATION ULTRASONIC HAND PIECE

(75) Inventors: Yuichirou Satou, Kawasaki (JP); Hidefumi Ota, Kawasaki (JP)

(73) Assignee: Miwatec Incorporated, Kawasaki (JP)

( * ) Notice: Subject to any disclaimer, the term of this patent is extended or adjusted under 35 U.S.C. 154(b) by 676 days.

(21) Appl. No.: 10/118,572

(22) Filed: Apr. 8, 2002

(65) Prior Publication Data

US 2003/0125620 A1 Jul. 3, 2003

(30) Foreign Application Priority Data

Dec. 27, 2001 (JP) ........................................ 2001-397028

(51) Int. Cl.[7] .............................................. A61B 17/22
(52) U.S. Cl. ......................................... 606/169; 604/22
(58) Field of Search ................................ 606/169, 170, 606/174, 176, 180, 159; 604/22, 44, 47, 52

(56) References Cited

U.S. PATENT DOCUMENTS

| | | | |
|---|---|---|---|
| 5,342,380 A | * | 8/1994 | Hood .......................... 606/169 |
| 6,497,715 B2 | * | 12/2002 | Satou .......................... 606/169 |
| 6,666,875 B1 | * | 12/2003 | Sakurai et al. ............... 606/169 |

FOREIGN PATENT DOCUMENTS

JP          58-58034         6/1983

OTHER PUBLICATIONS

*Patent Abstracts of Japan*, Abstract and computer translation of Japanese Patent "Ultrasonic Operation Apparatus", Publication No. 08–336545, Dec. 24, 1996, Japanese Application No. 07–169333, Filed Jun. 13, 1995.

* cited by examiner

Primary Examiner—Kevin T. Truong
(74) Attorney, Agent, or Firm—Lipsitz & McAllister, LLC

(57) ABSTRACT

Problems to be Solved

Surgical operation or others excellent in operability, safety, operation efficiency and precision are realized by outputting a vertical-torsional composite vibration through conversion processing of the longitudinal vibration from an ultrasonic oscillation mechanism and reducing the displacement speed of the non-working plane in a female portion less than the speed of the working plane.

Means to Solve the Problem

A configuration, comprising an ultrasonic oscillation mechanism composed of a longitudinal vibration element, a backing plate and a front plate for generating an ultrasonic vibration, a horn coupled with the ultrasonic oscillation mechanism for amplifying the vibration transmitted from said ultrasonic oscillation mechanism, a vibration conversion mechanism for converting the vibration transmitted from said ultrasonic oscillation mechanism into a composite vibration composed of a longitudinal vibration in the horn central axial direction and a torsional vibration having the horn central axis as fulcrum, and a female portion provided with a working plane and disposed at said horn tip, wherein said ultrasonic oscillation mechanism is composed of one or more groove portions formed on the circumferential surface of the horn or said backing plate, and a speed variation mechanism of torsional vibration in said composite vibration is formed in the female portion, in order to reduce the reciprocating rotation speed of the non-working plane less than the speed of the working plane.

12 Claims, 24 Drawing Sheets

Fig. 24
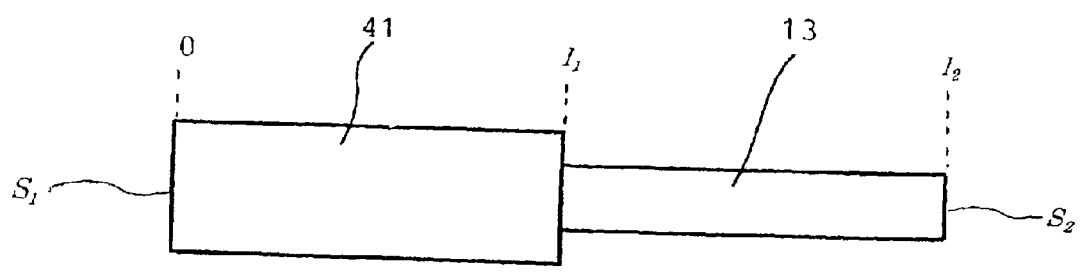
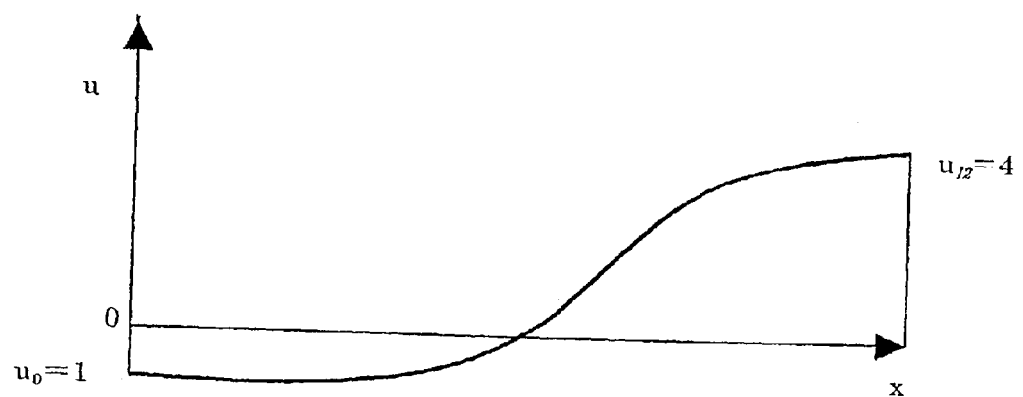

COUPLING VIBRATION ULTRASONIC HAND PIECE

DETAILED DESCRIPTION OF THE INVENTION

1. Field of the Invention

The invention of the present Application concerns a complex vibration ultrasonic hand piece, and more particularly, a complex vibration ultrasonic hand piece for reducing the reciprocating rotation speed of non working plane less than the speed of the working plane by generating a composite vibration composed of a longitudinal vibration in the horn central axial direction and a torsional vibration having the horn central axis as a fulcrum at a horn tip by converting the longitudinal vibration from a vibration source and, on the other hand, by forming a speed variation mechanism of torsional vibration in the composite vibration at the female portion of the horn tip.

2. Detailed Description of the Prior Art

Conventionally, the complex vibration ultrasonic hand piece has been used as one of various instruments of operation in the surgery domain, or as apparatus for processing of a variety of materials.

FIG. 10 shown a conventional complex vibration ultrasonic hand piece as operation instrument, configured to generate a high frequency by an ultrasonic wave oscillation circuit, and convert this high frequency electric power into a mechanical ultrasonic vibration of a female portion 4a by a hand piece 1 as shown in FIG. 10.

In short, the illustrated hand piece 1 comprises a built-in vibration mechanism 3 (electrostrictive element type, magnetostrictive type) as shown in FIG. 10(b) in a tubular member 2 composing the outer shell thereof, and the same is configured to be fixed to a horn 4 projecting from the tubular member 2.

The vibration mechanism 3 is composed of a vibrator 3a, a metallic backing plates 3b attached to both ends thereof and a front plate 3c, a high frequency electric power supplied from an ultrasonic oscillation circuit out of the drawing is converted into a mechanical vibration by the vibration mechanism 3, and this mechanical vibration is transmitted to a tip 4b of a horn 4 of a female portion.

Besides, in the drawing, 5 is an irrigation pipe for supplying an operation area with physiological saline or the like, and 6 is a suction pipe for collecting blood, excised fragments generated along with the operation, or others from a suction port 4b. It should be appreciated that, in place of the suction pipe 6, a suction duct 3d communicating with the suction port 4b is sometimes formed at the middle portion of the vibration mechanism 3 as shown in FIG. 10(c), to combine the cooling function of the vibration mechanism 3 at the same time.

By the way, in the aforementioned conventional ultrasonic hand piece, the vibration of the horn tip becoming a working portion in the operation in a living body and the processing of various materials, or others is restricted by the vibration element constituting the ultrasonic oscillation mechanism. For example, in the case of so-called longitudinal vibration where the properties of the vibration element are parallel to the axial direction, it results in the generation of longitudinal vibration at the horn tip. However, in the surgical operation or the processing of various materials also, in addition to the longitudinal vibration, a so-called torsional vibration repeatedly rotating around the axle is required to the operation area in order to plan the efficiency of necessary works such as cutting or the like, or to perform sharply and smoothly a fine operation. Therefore, a configuration for obtaining a vertical-torsional composite vibration by composing the vibration element of the vibration mechanism with a longitudinal vibration element and a torsional vibration element may be devised; however, the structure of the ultrasonic oscillation mechanism becomes complicated and heavy, not only making the handling difficult but also increasing the load of the output system of high frequency electric power and creating problems not only in respect of manufacturing cost but also running cost, and therefore is not composed practical actually.

In addition, conventionally, a drill has been used for cutting hard tissues of a living body, and it is feared that nerves and vessels be caught by the drill rotation in an area where nerves, vessels or others are entangled complicatedly. Therefore, it can not be used in the vicinity of nerve or vessel, and cases where the operation was composed impossible were not rear.

Also, in the aforementioned conventional ultrasonic operation instrument by vertical direction vibration, as the whole horn (female portion) tip displaces by an identical speed, the whole horn (female portion) tip results in having an identical crushing force, cutting force. Consequently, it is necessary to secure the safety by attenuation limitation of the cutting force as for the periphery of the target area, and processing only the target area with a predetermined cutting force.

SUMMARY OF THE INVENTION

The invention of the present Application intends to solve the aforementioned by a complex vibration ultrasonic hand piece, comprising an ultrasonic oscillation mechanism composed of a longitudinal vibration element, backing plates attached to both ends thereof and a front plate for generating an ultrasonic vibration of a predetermined frequency, a horn coupled with this ultrasonic oscillation mechanism for amplifying the vibration transmitted from said ultrasonic oscillation mechanism, a vibration conversion mechanism for converting the vibration transmitted from said ultrasonic oscillation mechanism into a composite vibration composed of a longitudinal vibration in the horn central axial direction and a torsional vibration having the horn central axis as fulcrum, and a female portion provided with a working plane and disposed at said horn tip, wherein:

said ultrasonic oscillation mechanism is composed of one or more groove portions formed on the external surface of any of the horn, the ultrasonic oscillation mechanism or a member interposed between the horn and the ultrasonic oscillation mechanism.

Also, it intends to solve the aforementioned by said composition wherein said horn is composed of a horn of ½ wavelength or more, and a converter mechanism of torsional vibration in said composite vibration is formed in said female portion, for reducing the reciprocating rotation speed of non working plane less than the speed of the working plane.

In the aforementioned composition, the groove portions are sometimes juxtaposed in plurality, said speed variation mechanism of reciprocating rotation in the female portion is composed of a projection portion formed on a shaft portion side face of the female portion, and a working plane is provided at a projection portion tip plane for reducing the torsional vibration speed of the non working plane less than the speed of the working plane.

Also, in any of the aforementioned respective compositions, said groove portions are sometimes juxtaposed in plurality, the speed variation mechanism of reciprocating rotation in the female portion is composed of a curved surface body having a small diameter portion and a large diameter portion formed on a tip of the female portion, and a working plane is provided on the large diameter portion for reducing the torsional vibration speed of the non working plane less than the speed of the working plane.

Moreover, in the foregoing, said curved surface body is sometimes composed of a sphere or a pseudo sphere.

Also, the curved surface body is sometimes composed of a spindle or a pseudo spindle.

In any of the aforementioned respective compositions, the groove portion is sometimes formed spiral.

Further, in any of the aforementioned respective compositions, said groove portion is has a predetermined deflection angle α, and this deflection angle is sometimes set to 0<α<90 degrees.

Also, in any of the aforementioned respective compositions, the groove portion is sometimes disposed in the vicinity of the loop position of the torsional vibration.

In any of the aforementioned respective compositions, a torsional vibration attenuation means is sometimes provided between the groove portion and an electrostrictive element of the ultrasonic oscillation mechanism, and this torsional vibration attenuation means is composed of a circumferential surface portion of a diameter larger than the circumferential surface portion where the groove portion is formed. Besides, this torsional vibration attenuation means is composed of a buffer having a cross-section larger than the cross-section (longitudinal portion in respect to the axial direction) in the groove portion, and the portion shape of the buffer may be formed square, circular, or various others forms.

Further, in any of the aforementioned respective compositions, the vibration conversion mechanism comprises sometimes a body detachably interposed between the horn and the ultrasonic oscillation mechanism and a groove portion formed around the body circumferential surface.

Figure 3:
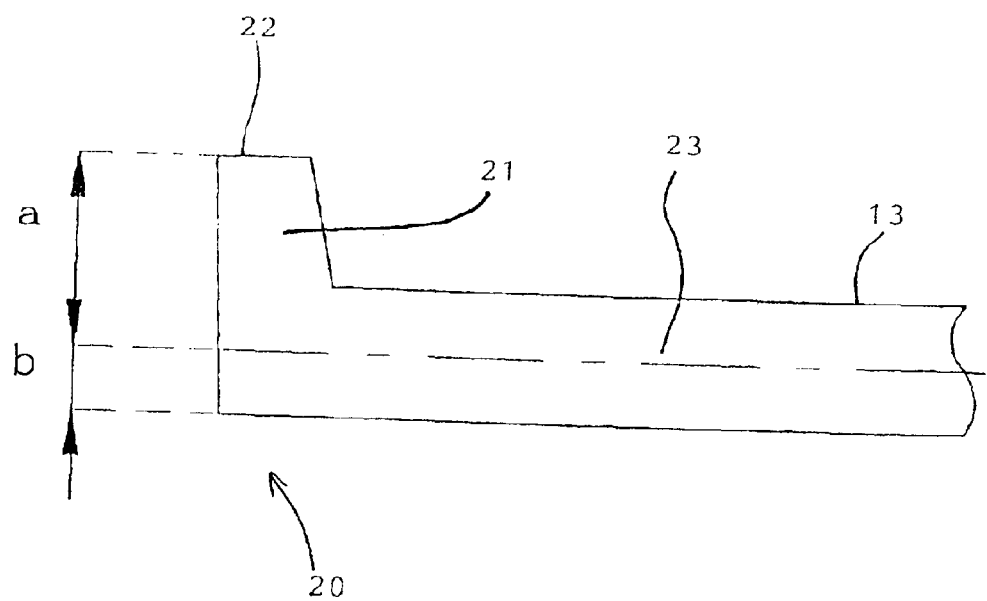
FIG. 3 is an enlarged view of a female portion having a speed variation mechanism.
Figure 4:
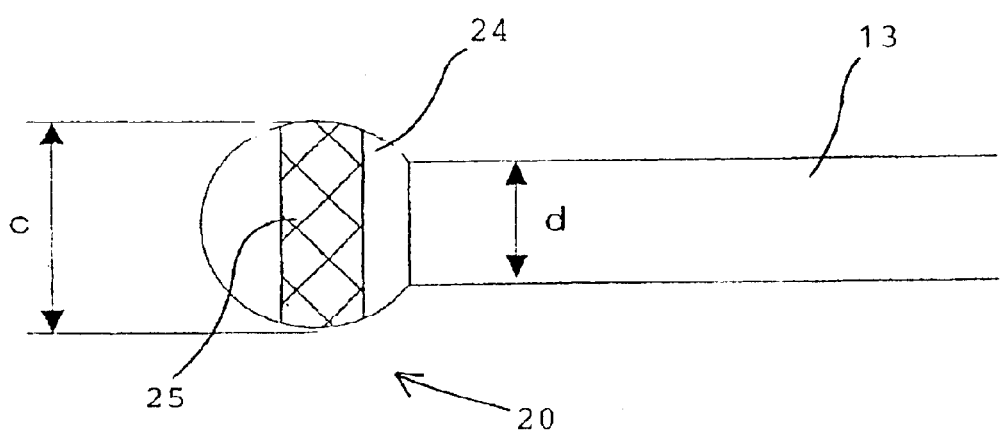
FIG. 4 is an enlarged view of the female portion according to another embodiment.
Figure 11:
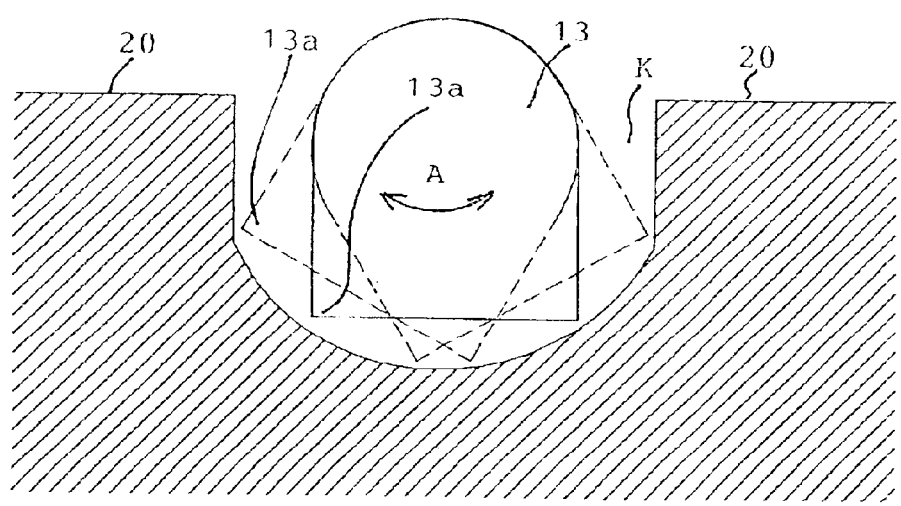
Figure 12:
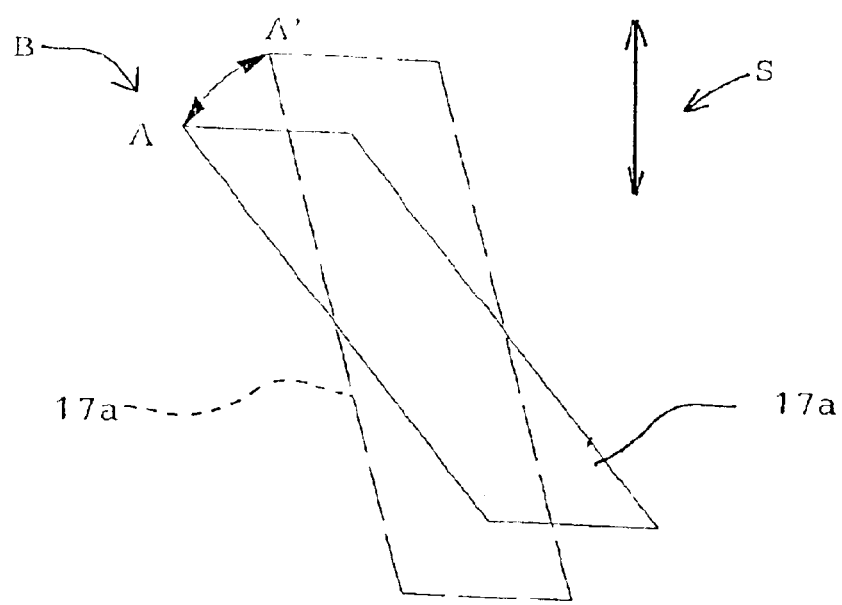
Figure 13:
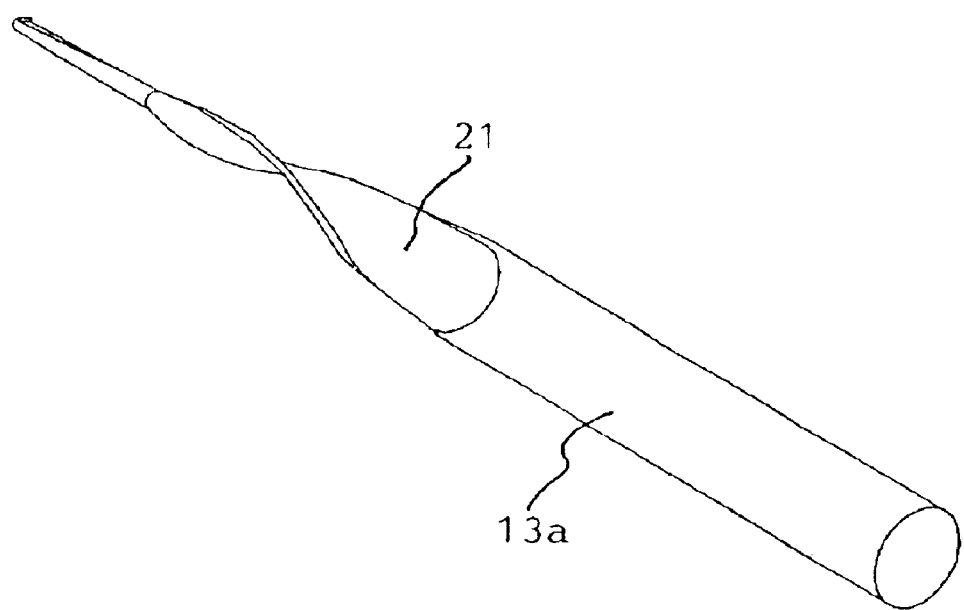
Figure 14:
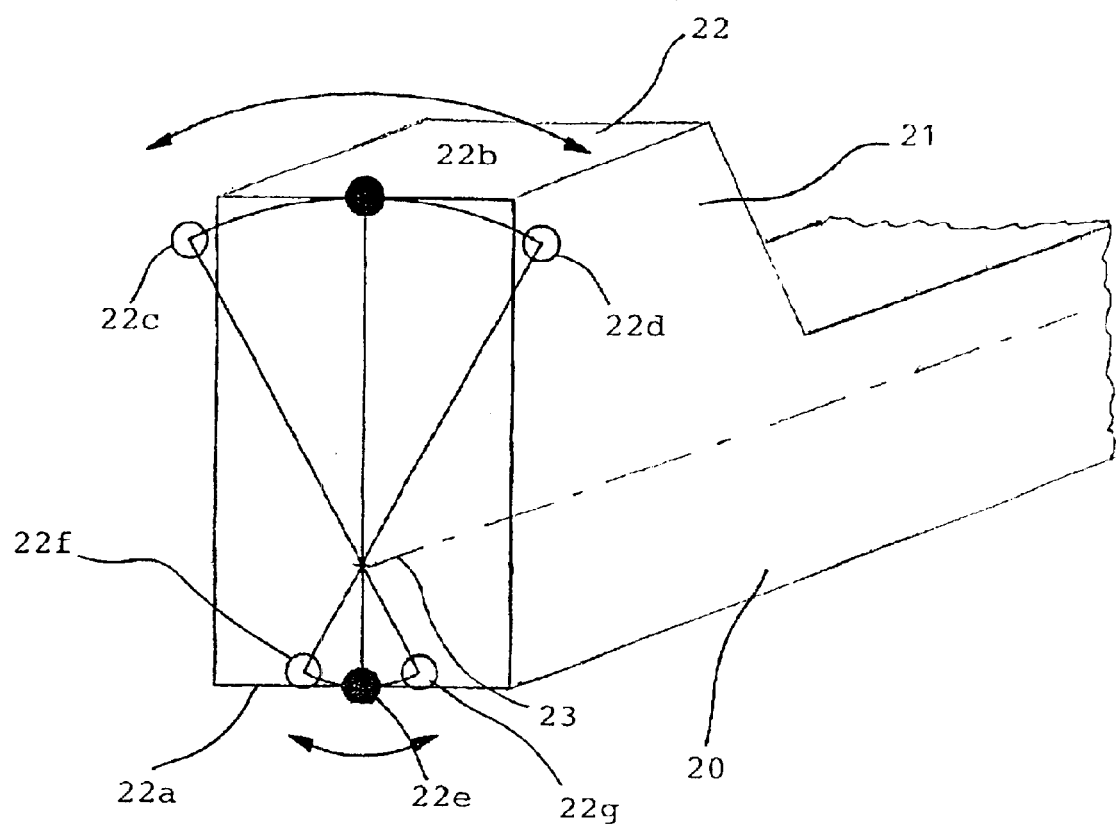
Figure 15:
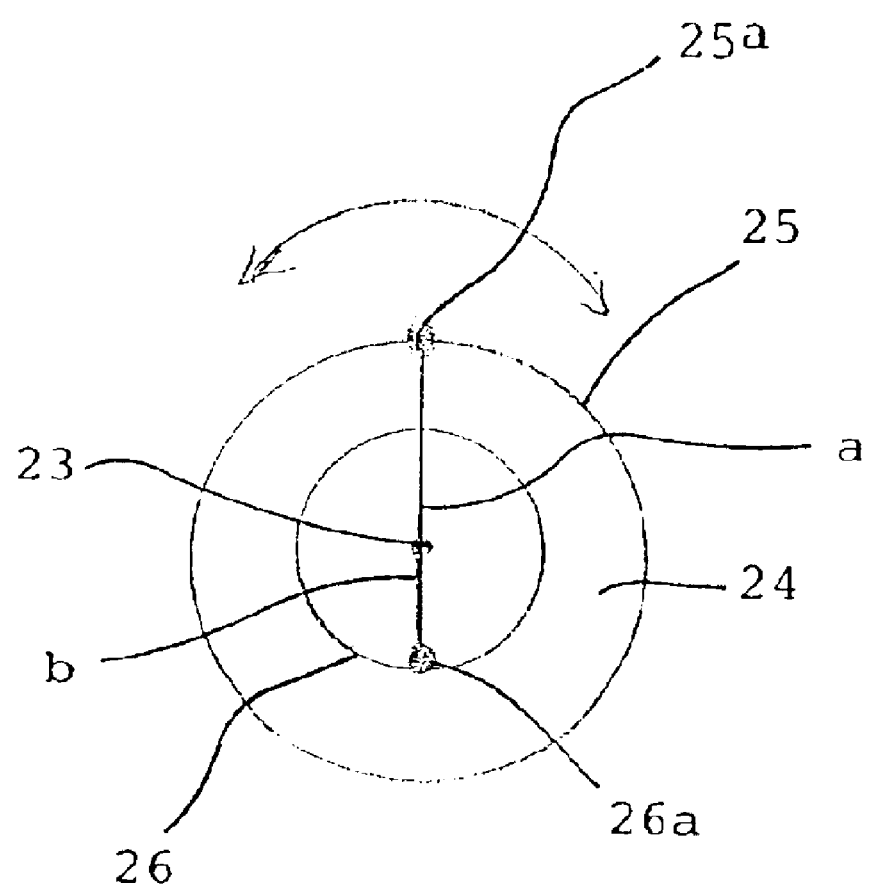
Figure 16:
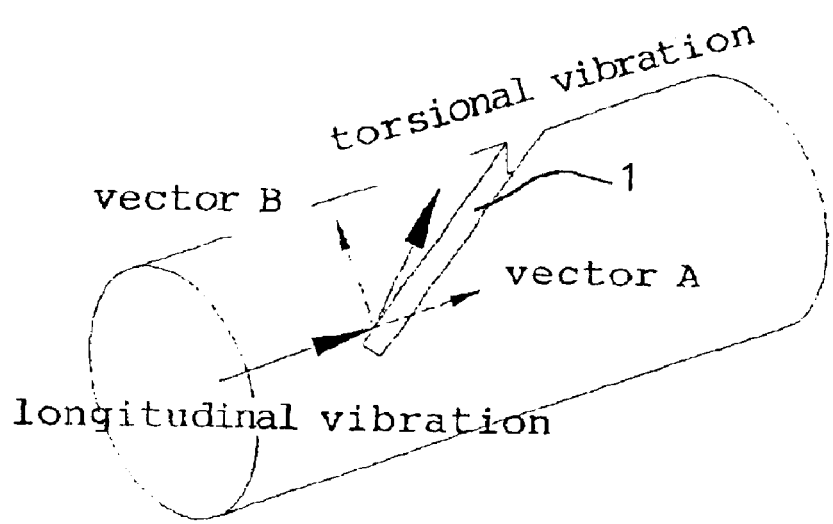
Figure 17:
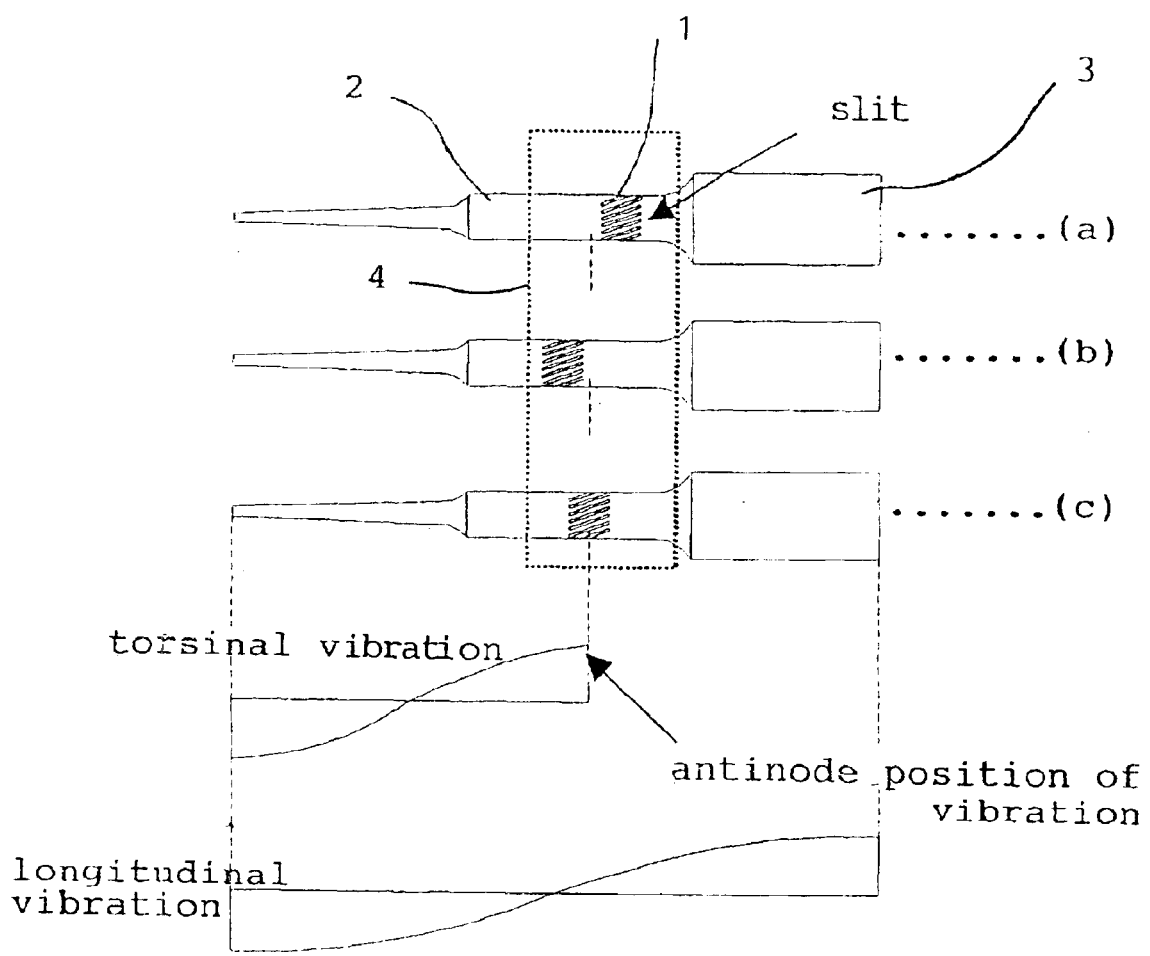
Figure 18A:
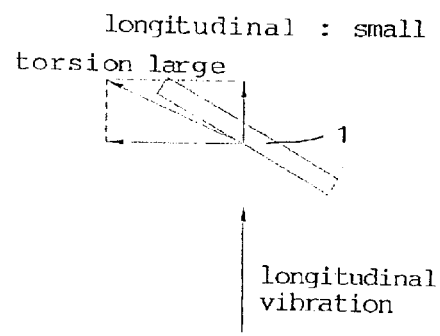
Figure 18B:
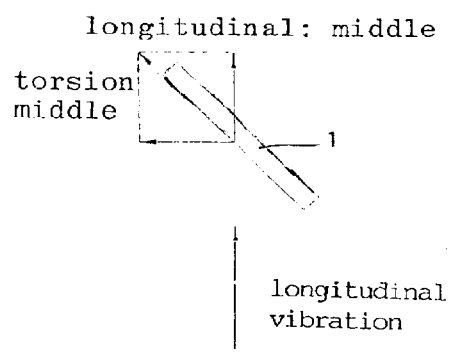
Figure 18C:
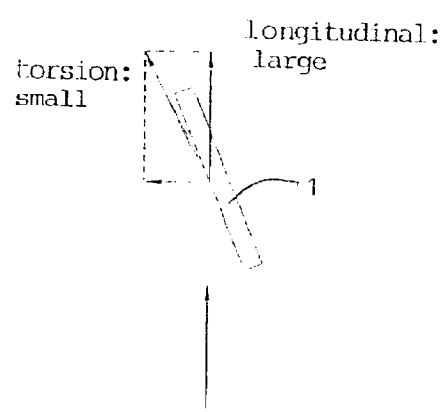
Figure 19:
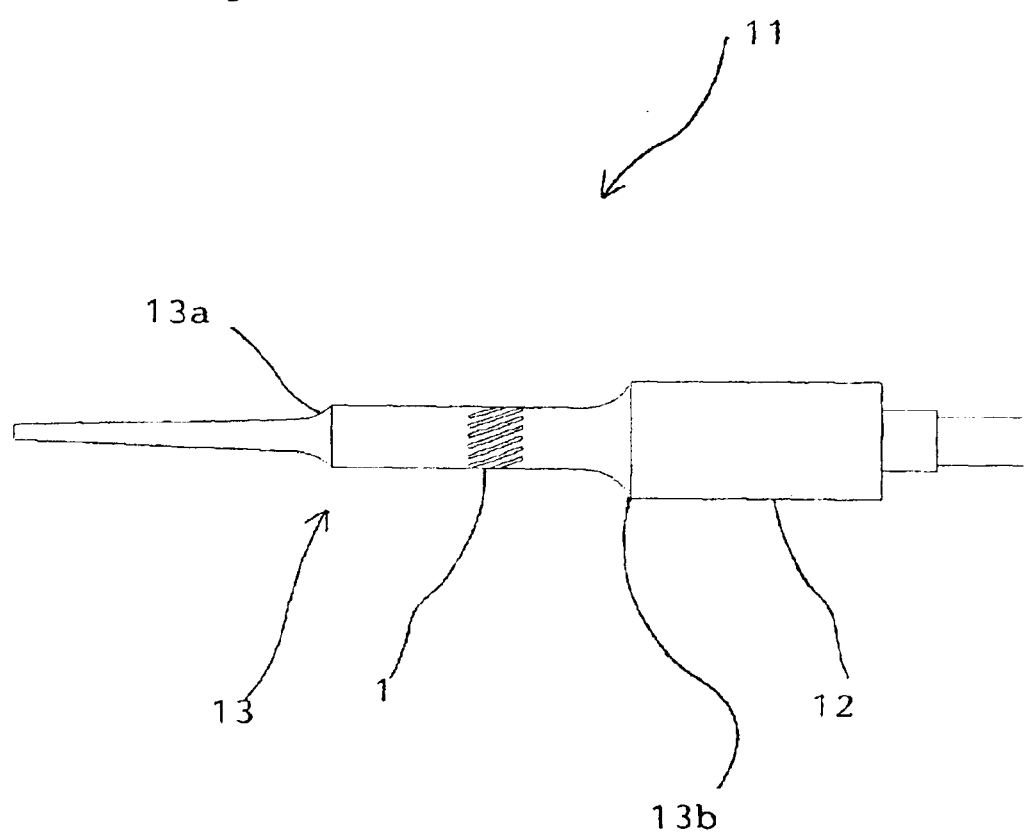
Figure 20:
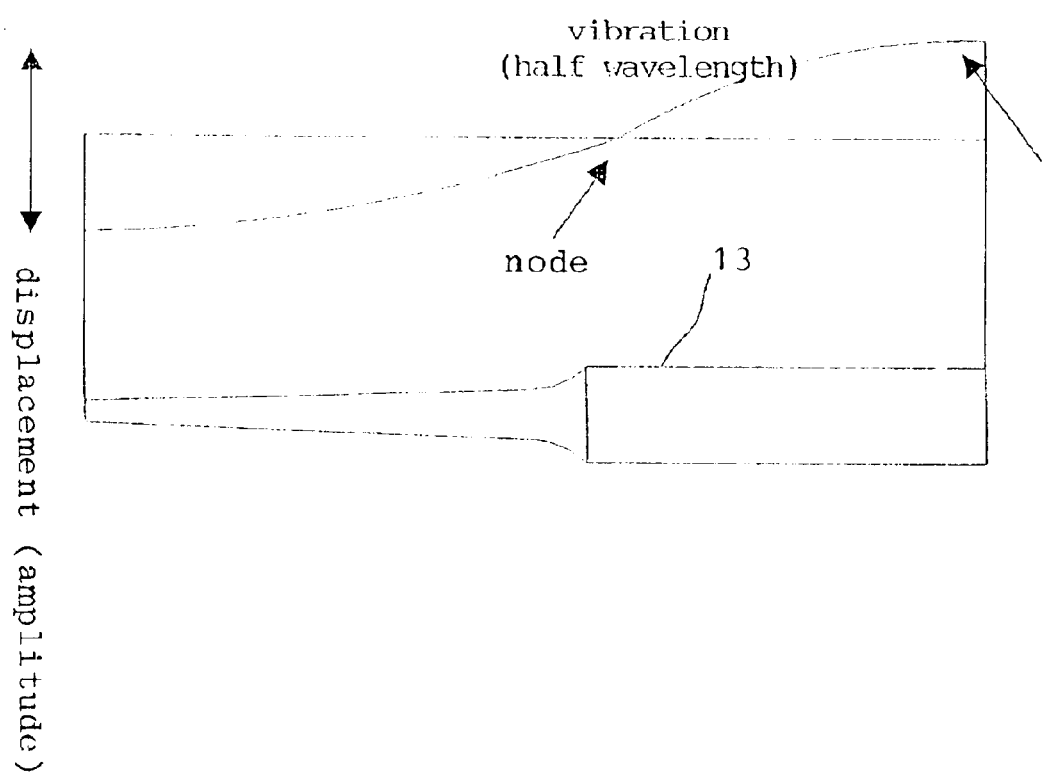
Figure 21:
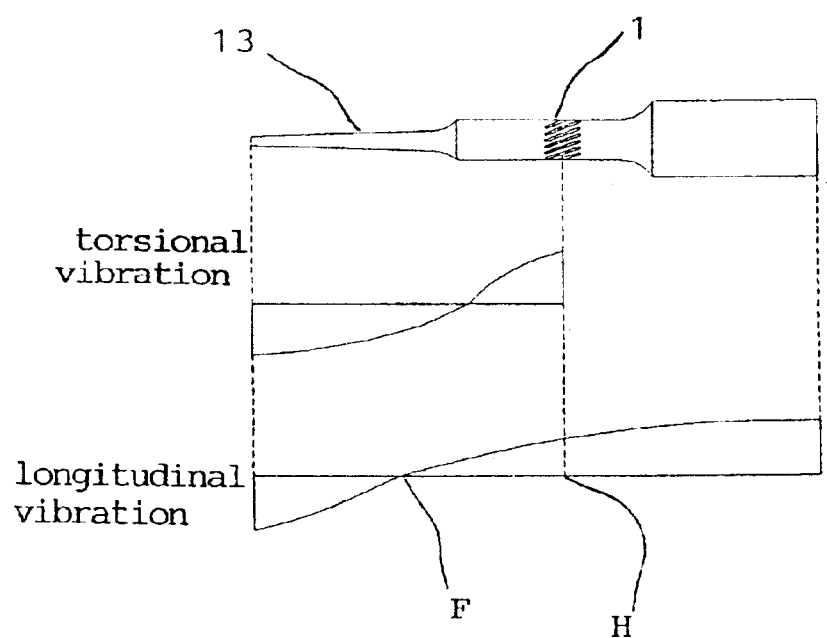
Figure 22:
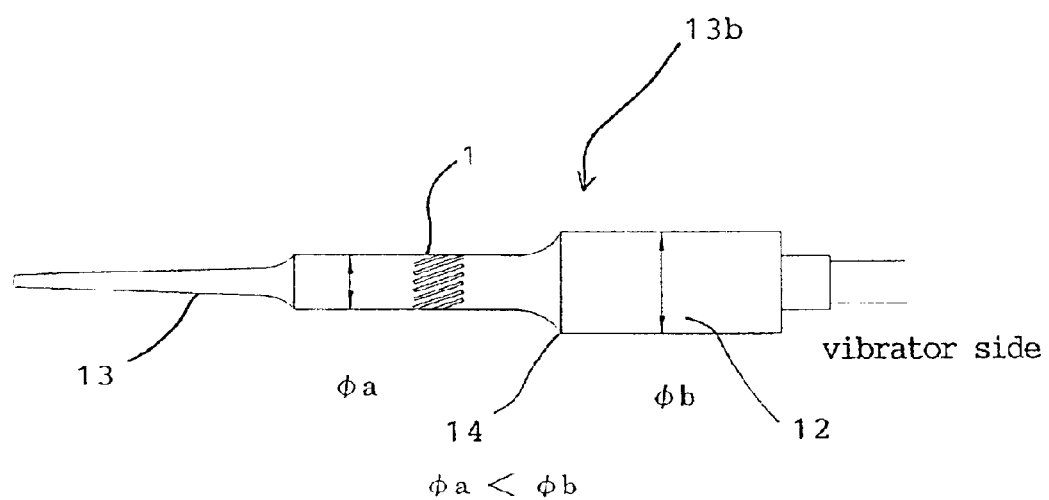
Figure 23:
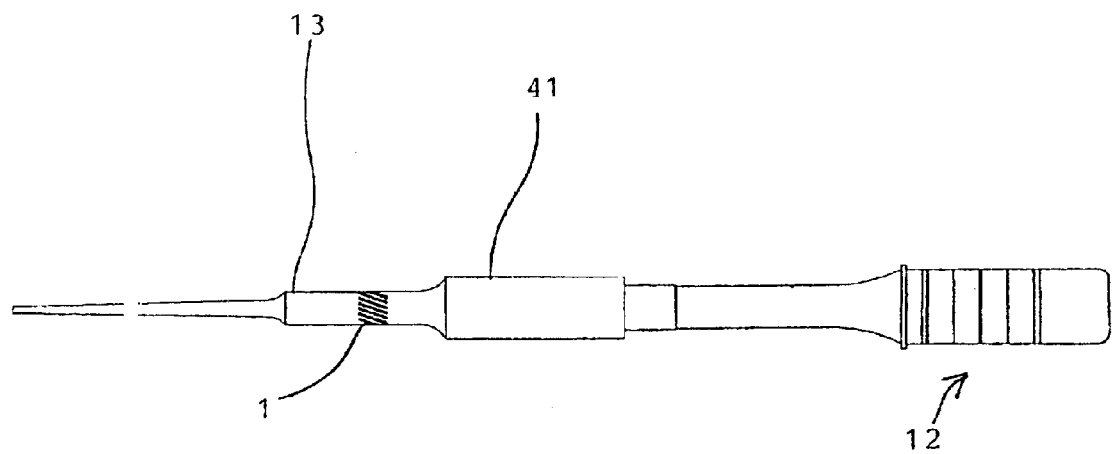

A partially omitted side view of the ultrasonic hand piece showing a second embodiment;

FIG. 11 is a schematic drawing showing the cutting operation of a live bone by the ultrasonic hand piece (ultrasonic scalpel) according to the invention of the present Application;

FIG. 12 illustrates the conjecture principle of vibration conversion;

FIG. 13 is a perspective view of an ultrasonic horn having an ultrasonic oscillation mechanism by a helical body;

FIG. 14 illustrates the operation of the female portion shown in FIG. 3;

FIG. 15 illustrates the operation of the female portion shown in FIG. 4;

FIG. 16 is a schematic drawing showing the generation of torsional vibration;

FIG. 17 shows the correlation of the position of the groove portion, longitudinal vibration, and torsional vibration:

FIG. 18 is a schematic drawing showing the variation of proportion of longitudinal vibration and torsional vibration in case of various changes of the deflection angle α in respect to the horn central axis of the groove portion 1;

FIG. 19 is a side view of the ultrasonic hand piece according to a fifth embodiment;

FIG. 20 shows the relation between horn length and longitudinal vibration wavelength;

FIG. 21 shows the relation between horn length, torsional vibration loop position and respective vibration wavelength;

FIG. 22 illustrates a torsional vibration attenuation means;

FIG. 23 illustrates another embodiment of torsional vibration attenuation means; and FIG. 24 illustrates the principle of torsional vibration attenuation.

DETAILED DESCRIPTION OF THE PREFERRED EMBODIMENT

Embodiments of the invention of the present Application will be described below.

Figure 1:
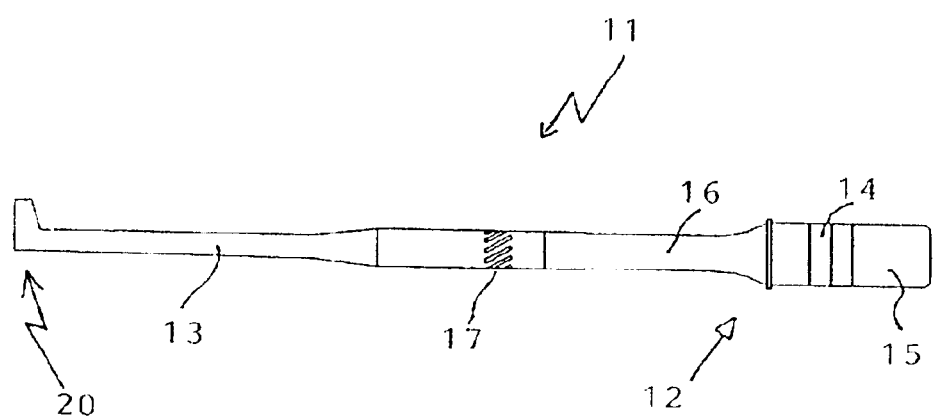
FIG. 1 is a side view of the ultrasonic hand piece according to a first embodiment.

FIG. 1 is a side view of the ultrasonic hand piece according to a first embodiment of the invention of the present Application.

In the drawing, 11 is an ultrasonic hand piece, comprising an ultrasonic oscillation mechanism 12 and an ultrasonic horn 13 joined to the same, and they are inserted into a outer cylinder not shown. The ultrasonic oscillation mechanism 12 comprises a longitudinal vibration element 14, and a front plate 15 and a backing plate 16 placed at both ends thereof.

A vibration conversion mechanism 17 for converting the vibration transmitted from said ultrasonic oscillation mechanism 12 into a (vertical-torsional) composite vibration composed of a longitudinal vibration in the central axial direction of the ultrasonic horn 13 and a torsional vibration having the central axis of the ultrasonic horn 13 as fulcrum is provided in the vicinity of the end portion of the ultrasonic horn 13. Besides, 20 is a female portion provided at the tip of said ultrasonic horn 13.

Figure 2:
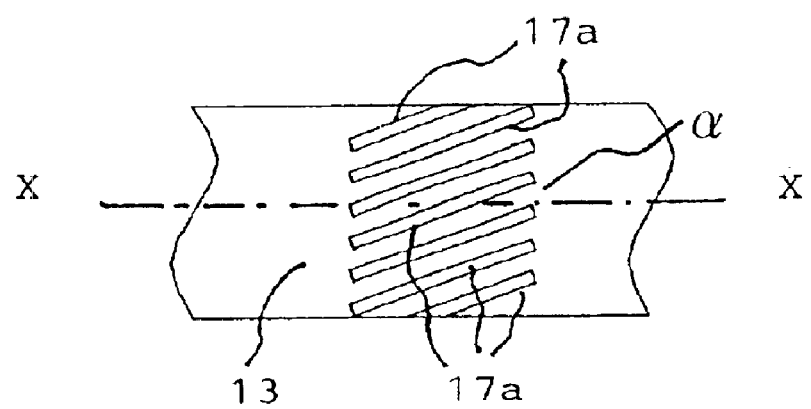
FIG. 2 is a enlarged view of essential parts of FIG. 1.

The vibration conversion mechanism 17 is, in the embodiment, composed of a plurality of groove portions 17a formed to be wound around the circumferential surface of the ultrasonic horn 13 as shown in FIG. 2.

These plurality of groove portions 17a are carved in parallel with a predetermined interval respectively and have a predetermined deflection angle α with the central axis X—X of the ultrasonic horn 13 on the circumferential surface, and this deflection angle α is set in a range of 0 degree<α<90 degrees.

Besides, the shape of the groove portion 17a is rectangular, and the width thereof is set to a range of 0.5 to 5 mm, the length 3 to 30 mm and the depth 0.5 mm or more It should be appreciated that the set position of the groove portion as vibration conversion mechanism 17 is not limited to the horn circumferential surface, but it can be formed on the outside face of any one of the horn, sound wave oscillation mechanism between the horn tip and the electrostrictive element thereof or members interposed between the horn and the sound wave oscillation mechanism.

FIG. 3 is an enlarged view of said female portion 20 and, in the drawing, 21 is a projection portion as speed variation mechanism and, is formed on the shaft side face of the female portion 20. A working plane 22 is formed on a tip face of the projection portion 21 is formed for cutting hard tissues or others by composite vibration. It should be appreciated that a indicates the distance between the working plane 22 and the central axis 23 of the torsional vibration, b the distance between the shaft side face of the female portion 20 and said central axis 23, and it is set to a>b.

FIG. 4 is an enlarged view of the female portion 20 according to another embodiment. 24 is a curved surface body as speed variation mechanism of torsional vibration, and here, a sphere is used as curved surface body, and a working plane 25 is formed all around the large diameter portion (vicinity thereof including the diameter portion) of this sphere 24.

The working plane 25 has a surface formed into a rough particulate or file shape in order to facilitate cutting operation or others of a hard tissue. The portion other than the working plane 25 of the sphere 24 surface, namely non working plane, is formed smooth in order to prevent damage to the nerve, vessel, or the like during the intervention operation or others. It should be appreciated that c indicates the diameter of the sphere 24, d the diameter of the shaft of the female portion, and they are set to c>d.

Figure 5:
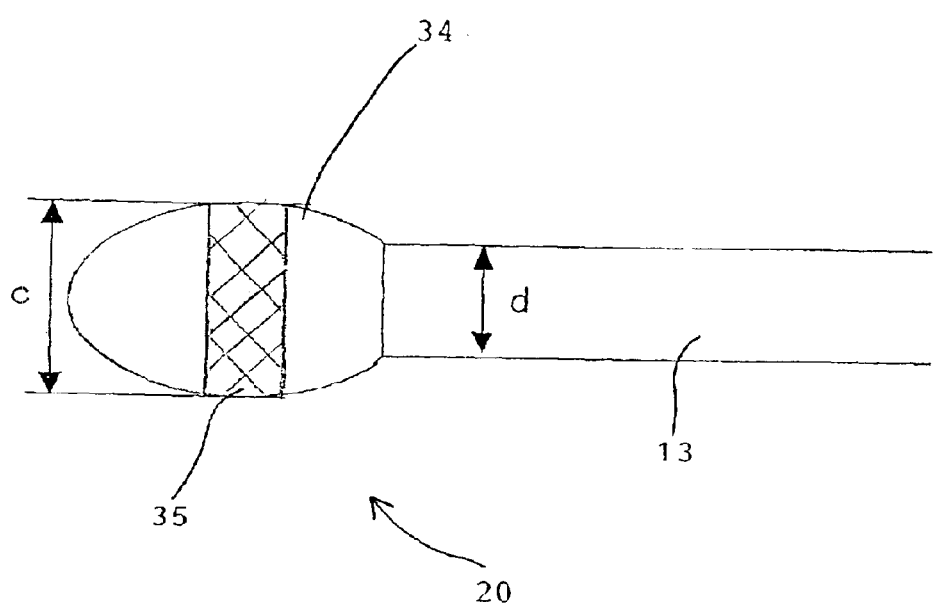
FIG. 5 is an enlarged view of the female portion according to another embodiment.

In the foregoing, though an example of composing the curved surface body with a sphere has been mentioned, a spindle 34 as shown in FIG. 5 or one having a shape similar to the same can also be used as this curved surface body.

A working plane 35 is formed all around at the middle portion of the spindle 34.

The working plane 35 has a surface formed into a rough particulate or file shape in order to facilitate cutting operation or others of a hard tissue. The portion other than the working plane 35 of the spindle 34 surface, namely non working plane, is formed smooth in order to prevent damage to the nerve, vessel, or the like during the intervention operation or others.

Figure 6:
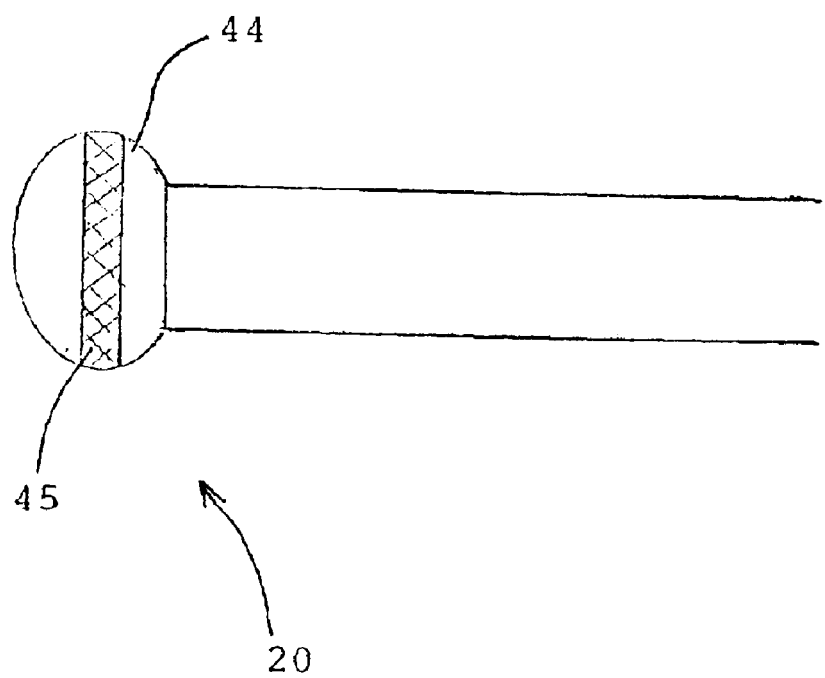
FIG. 6 is an enlarged view of the female portion according to another embodiment.

It should be appreciated that a body similar to the spindle as shown in FIG. 6 can also be used as this curved surface body. In short, in FIG. 6, 44 is a body having an elliptical portion to be used as curved surface body, and a working plane 45 is formed all around at the middle portion thereof. And, the portion other than the working plane 45 of this curved surface body 44 surface, namely non working plane, is formed smooth in order to prevent damage to the nerve, vessel, or the like during the intervention operation or others.

Figure 7:
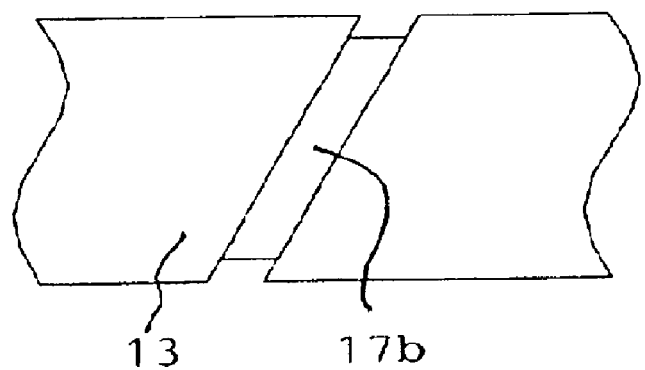
FIG. 7 is a partially omitted side view of the ultrasonic hand piece showing a second embodiment.

On the other hand, as for vibration conversion mechanism 17, in the embodiment mentioned above, a case of composing with a plurality of juxtaposed groove portions; however, this groove portion may be composed of a single groove 17b formed to surround the surface of the ultrasonic horn 13 as shown in FIG. 7. However, this groove 17b also has a predetermined deflection angle α with the central axis of the ultrasonic horn 13 on the circumferential surface, and this deflection angle α is set in a range of 0 degree<α<90 degrees. And, the width and depth of this groove 17b are also set to ranges of 0.5 to 5 mm, 0.5 mm or more respectively, similarly to said embodiment.

Figure 8:
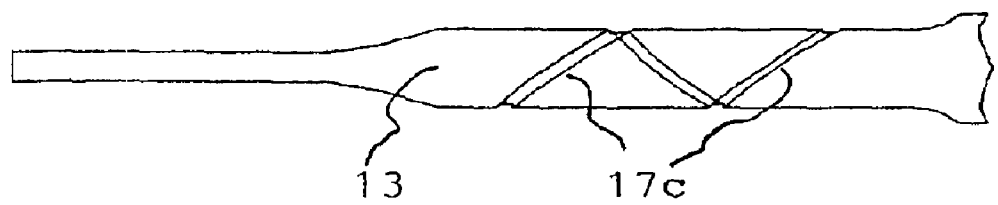
FIG. 8 is a side view of the ultrasonic horn according to a third embodiment.

FIG. 8 is a side view of the ultrasonic horn according to a second embodiment.

In this embodiment, the vibration conversion mechanism 17 is composed of a spiral groove portion 17c formed to surround the surface of the ultrasonic horn 13. And, this groove 17c also has a predetermined deflection angle α with the central axis of the ultrasonic horn 13 on the circumferential surface similarly to the forgoing, and this deflection angle α is set in a range of 0 degree<α<90 degrees.

Besides, the groove width and depth are also set to ranges of 0.5 to 5 mm, 0.5 mm or more respectively, similarly to said embodiment.

Figure 9:
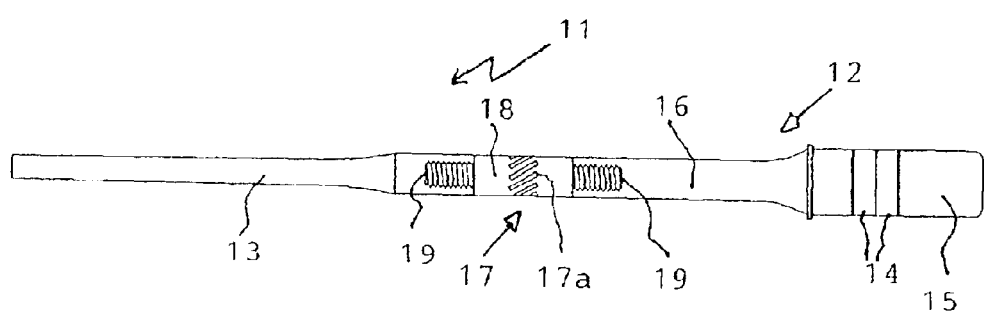
FIG. 9 is a side view of the ultrasonic horn according to a fourth embodiment.

FIG. 9 is a side view of the ultrasonic horn according to a third embodiment.

In this embodiment, the vibration conversion mechanism 17 is composed of a body 18 interposed detachably between the ultrasonic horn 13 and the ultrasonic oscillation mechanism 12 and one or more groove portions 17a formed on this body 18 circumferential surface as illustrated.

The body 18 is coupled respectively detachably by a backing plate 16 and bolts 19, 19 in the ultrasonic horn 13 and the ultrasonic oscillation mechanism 12 as illustrated. The embodiment, allowing to remove simply the vibration conversion mechanism 17, has an advantage that it is enough to remove the vibration conversion mechanism 17 and connecting directly the ultrasonic horn 13 and the ultrasonic oscillation mechanism 12, for instance, in case of desiring to use only with longitudinal vibration.

In FIG. 9, the groove portion to be formed in the body 18 are composed of a plurality of parallel groove portions 17a formed to surround the circumferential surface of the body 18; however, as shown in FIG. 7, FIG. 8 concerning respective embodiments mentioned above, it may composed of a single groove 17b formed to surround the surface of the body 18 or a spiral groove portion 17c formed to surround the surface of the body 18.

Figure 10:
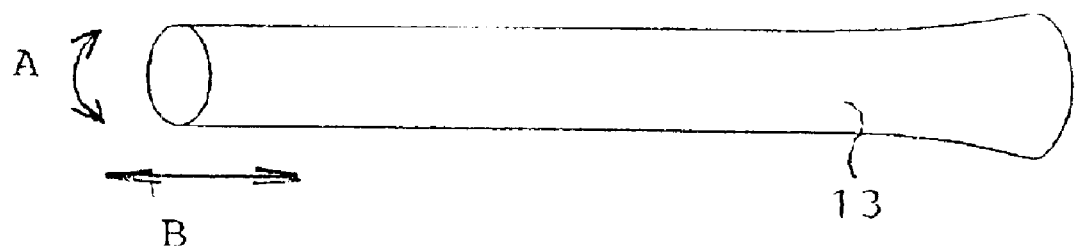
FIG. 10 is a perspective view showing the movement at the tip of the ultrasonic horn 13.

FIG. 10 is a drawing showing the movement at the tip of the ultrasonic horn 13, the tips of the ultrasonic horn 13 results in performing a rapid reciprocating rotation (torsional vibration) in the arrow A direction around the central axis and, on the other hand, a rapid reciprocating movement (longitudinal vibration) in the arrow B direction along the central axis, through composition of longitudinal vibration and torsional vibration generated by converting the longitudinal vibration in the vibration conversion mechanism 17.

Acquisition of the aforementioned composite movement at the tip of the ultrasonic horn 13 results in bringing a great advantage, for instance, to cut a live body bone in the surgical operation or others.

In short, saw type, rotating drill type or other operation instruments have been used often to out a live body bone in the related art; however, an ultrasonic scalpel is appropriate for regions where nervous tissues, blood vessels or others are feared to be damaged.

Nonetheless, as the conventional ultrasonic scalpel moves reciprocally along the axial direction, in case where the scalpel point invades the depths of a tissue, the side portion of the scalpel comes into contact with the tissue and will be compressed, attenuating the movement of the scalpel.

Whereas, in the ultrasonic horn according to the invention of the present Application, as a rapid reciprocating rotation and a rapid reciprocating movement are composed at the tip thereof, live bone cutting or others can be performed extremely smoothly. In short, FIG. 11 is a schematic diagram showing the live bone cutting operation by an ultrasonic hand piece (ultrasonic scalpel) according to the invention of the present Application and, as a torsional vibration is output to a scalpel (horn) 13 tip in addition to a longitudinal vibration, a rapid reciprocating rotation (torsional vibration) is generated in the arrow A direction at the scalpel (horn) 13. Consequently, a side end portion 13a of the scalpel (horn) 13 tip cuts the live bone, and a gap K is formed between the scalpel (horn) 13 tip and the live bone, allowing to perform the cutting extremely smoothly even for the cutting in the depths of a live bone. In addition, the cutting function by the longitudinal vibration of the scalpel tip, accompanying a torsional moment, not only improves considerably the tissue shearing efficiency, but also realizes a cutting in a clean state, because the definition or so-called sharpness in the cutting function is improved remarkably, and the tissues in the cutting area do not collapse or else.

In the foregoing, though the case of surgical operation has been described, it is not restrictive, and it goes without saying that similar effects may be expected in the processing of various materials.

Figure 12B:
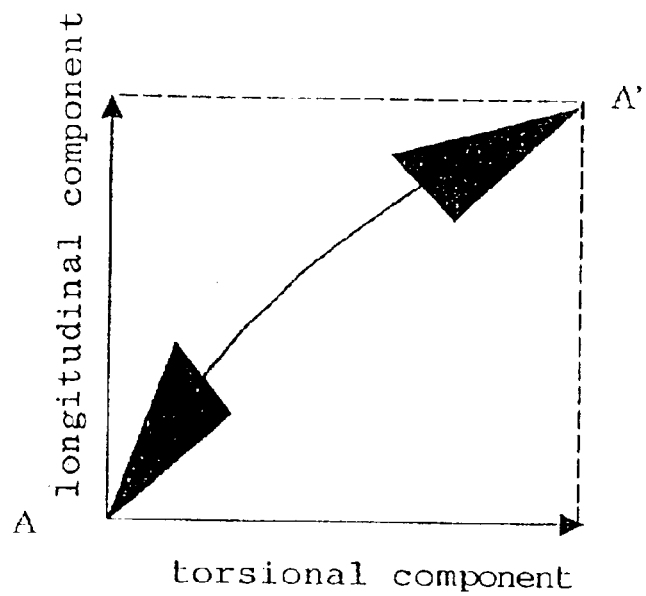

The whole picture of the mechanistic function of the vibration conversion mechanism according to the invention of the present Application is being revealed through analysis of various experimental data, and the vibration conversion function by the groove portion can be conjectured as follows at the present point of time. It is supposed that the groove portion 17a repeats the deformation due to the longitudinal vibration as shown in FIG. 12, and a part of components in the vertical direction is converted into the torsional direction during this deformation. In short, in FIG. 12(a), an effort due to the longitudinal vibration shown by the arrow S acts on the groove portion 17a; consequently, the groove portion 17a results in repeating the deformation from a state shown by the solid line to a state by the dotted line. If this is shown by specific points, a corner portion A of the groove portion 17a repeats the reciprocation movement between the home position and the A' point. And this results in generation of the same in all areas of the groove portion. FIG. 12(b) is a drawing where the locus of said corner portion A is represented in a graph taking the Y-axis as vertical direction movement and the X-axis as transversal direction movement of the locus of said corner portion A. According to this, the corner portion A moves reciprocally between the origin and the A' point all the way moving in the transversal direction in addition to the vertical direction, and it is understood that a reciprocating movement in the transversal direction generates as torsional vibration component.

Thereby, a composite vibration due to the longitudinal vibration and torsional vibration is generated in the body 18, and this composite vibration comes to be output at the tip of the ultrasonic horn.

At this stage, it is ascertained by experiments that the following conditions influence the composite vibration due to the longitudinal vibration and torsional vibration that can be obtained at the tip of the ultrasonic horn, and detailed data is being collected for the moment to construct a relation between the conditions and the composite vibration.

a: Groove depth, length, depth and angle with the central axis
b: Position in groove axial direction
c: Shape of ultrasonic horn
d: Number of groove It should be appreciated that it was found that the vibration conversion can also be obtained by a helical body shown in FIG. 13. In the drawing, 21 is an integrally formed helix portion in an ultrasonic horn 13a.

FIG. 14 illustrates the operation of the female portion 20 shown in FIG. 3. A projection portion 21 as speed variation mechanism of torsional vibration, make a torsional vibration around the central axis 23 of the torsional vibration as illustrated, but the displacement speed of a non-working plane 22a becomes lower than a working plane 22. In short, a fixed point 22b on the working plane 22, rotates reciprocally between points 22c and 22d. Contrarily, On the other hand, a fixed point 22e of the non-working plane 22a corresponding said fixed point 22b, rotates reciprocally with points 22f and 22g. On the other hand, as shown in FIG. 3, the distance between the fixed point 22b of the working plane 22 and the central axis 23 is a, the distance between the fixed point 22e of the nonworking plane 22a and the central axis 23b and a>b, the displacement speed of the fixed point 22b of the working plane 22 becomes a/b times of the displacement speed of the fixed point 22e of the non-working plane 22a.

Thus, the torsional vibration speed of the non-working plane 22 is reduced by the projection portion 21 as speed variation mechanism. Therefore, the crushing force of the non-working plane 22 becomes weaker than the working plane 22, and the possibility of damaging areas other than a predetermined area with the non-working plane 22 is reduced, during cutting, crushing or other operations of the predetermined area by the working plane 22.

FIG. 15 illustrates the operation of the female portion 20 shown in FIG. 4.

As mentioned before, 24 is a sphere as speed variation mechanism of torsional vibration and a working plane 25 is formed all around the large diameter portion (vicinity thereof including the diameter portion) of this sphere 24. Now, if the torsional vibration is compared between a fixed point 25a on the working plane 25 and a fixed point 26a of an arbitrary non-working plane 22a, the vibration speed of the fixed point 26a is smaller than the fixed point 25a. In short, when the fixed point 25a moves a distance L in a time t around a circumference with the radius a (distance between the fixed point 25a and the rotation center 23), as the fixed point 26a moves a distance L2 in a time t around a circumference with the radius b (distance between the fixed point 26a and the rotation center 23), the reciprocating rotation speed of the working plane 22 becomes a/b times of the speed of a circle 26. Thus, the speed of the nonworking plane is lower than the working plane, and the crushing force or others also become weak.

In addition, as the working plane 25 formed all around the circumference with a predetermined width about the diameter portion of the sphere, cutting, crushing or other operations can be performed in all directions of 360 degrees.

Then, as mentioned above, the surface there of formed into rough granular or file shape to facilitate cutting operation or others of hard tissues. Besides, in addition to a gradual reduction of vibration speed, the non-working plane is formed smooth in a way to prevent damage of nerves, blood vessels or others in a surgical operation and so on.

It should be appreciated that the function of the female portion shown in FIGS. 5 and 6 are similar to the foregoing and a repeated description shall be omitted.

Further, a fifth embodiment shall be described.

In the invention of the present Application, as shown in a schematic diagram of FIG. 16, the torsional vibration is obtained by bending a part of the longitudinal vibration component and generating a vibration in a direction different from the vertical direction. In FIG. 15, when the longitudinal vibration component is bent in the torsional direction by the groove portion 1, this component becomes the composition of the vertical wave and the transversal wave; however, as it is difficult to represent this composition theoretically (mathematically), respective components of the vertical wave and the transversal wave are represented in a vector-like manner.

The groove portion for generating a torsional vibration from a longitudinal vibration is disposed in the vicinity of the loop position (including the vicinity thereof) of the torsional vibration as shown in FIG. 17. In the drawing, 2 is an ultrasonic horn composed of titanium alloy, 3 is a backing plate interposed between a (not shown) ultrasonic vibrator and an ultrasonic horn 1, and the groove portion is juxtaposed in plurality in a vicinity range 4 of the loop position of the torsional vibration, on the circumferential surface of the ultrasonic horn 1, and respective groove portion has a predetermined deflection angle α (0<α<90 degrees) in respect to the central axis of the horn.

FIG. 17 shows the correlation of the position of the groove portion, longitudinal vibration, and torsional vibration based on experimental results and, in FIG. 17(*a*), the groove portion 1 is placed slightly near the vibrator from the loop position of the vibration, and as shown, the torsional vibration frequency is lower than the case of loop position. Also, in FIG. 17(*b*), the groove portion 1 is placed at the loop position of the vibration, and in this case, respective vibration frequencies of the longitudinal vibration and the torsion agree, vertical-torsional vibrations coexist respectively, resulting in the acquisition of an optimal composite vibration.

As mentioned above, in order to obtain a composite vibration of vertical-torsional vibration in a preferable state, the coexistence of longitudinal vibration and torsional vibration is required and, for this effect, it is necessary to make respective characteristic frequencies agree substantially, and if this condition is largely destroyed, either vibration vanishes. It should be appreciated that a complete agreement of respective frequencies is not required and in the vicinity of the loop position where the agreement is achieved, when each frequency approaches there, it will be drawn into either one and the phenomenon of frequency agreement will occur.

By the way, the torsional vibration is a composite vibration of vertical wave (wave displacing in the vibration progression direction) and transversal wave (wave displacing perpendicularly to the vibration progression direction) and in case of vibrating with a same frequency, the length of half wavelength will be different due to the difference between the vertical wave speed and the transversal wave speed, and the length of half wavelength of the torsional vibration becomes shorter than the longitudinal vibration. Consequently, in order to obtain a preferable composite vibration (torsional vibration) as mentioned above it is necessary to make agree frequencies of the longitudinal vibration and torsional vibration, in the designing of the tip (horn and backing plate) for generation torsional vibration, and by this condition, the set position of the groove portion will automatically be the predetermined position, namely the torsional vibration loop position.

If the groove portion 1 is disposed in the vicinity of the torsional vibration loop position, the proportion of longitudinal vibration and torsional vibration can be converted variously, by changing the nature and shape of the groove.

In short, FIG. 18 is a schematic diagram showing the variation of proportion of longitudinal vibration and torsional vibration in case of various changes of the deflection angle α in respect to the horn central axis of the groove portion 1.

In FIG. 3, it is set to α=60 degrees for (a), α=45 degrees for (b) and α=20 degrees for (c). According to the experiment, the longitudinal vibration and torsional vibration balance for (b), the torsional vibration is superior for (a), and on the contrary, the longitudinal vibration surpasses the torsional vibration for (c). Based on these results, it can be conjectured that the angle of the groove portion is also connected to the generation mechanism of torsional vibration.

Also, it is conjectured that the depth of the groove portion influences the generation mechanism of torsional vibration. In short, in case of considering the portion of the circumferential surface where the groove portion is formed, the deeper is the groove portion, the more is the longitudinal vibration component crossing with the groove portion, and consequently, the conversion quantity into torsional vibration increases; in other words, the deeper is the groove portion, the more becomes the torsional vibration component.

Similarly to the foregoing, length, number or others of the groove portion also become factors to influence the proportion of longitudinal vibration and torsional vibration.

FIG. 19 is a side view of the ultrasonic hand piece according to said embodiment. In the drawing, 11 is an ultrasonic hand piece, comprising an ultrasonic oscillation mechanism 12 and an ultrasonic horn 13 joined to the same, and they are inserted into a now shown outer cylinder.

The ultrasonic oscillation mechanism 12 is the one of a well-known configuration having a longitudinal vibration element and a front plate and a backing plate placed at both ends thereof. It should be appreciated that 13*a*, 13*b* are respectively a restriction portion and a torsional vibration attenuation means mentioned below.

A plurality of groove portion 1 for converting the vibration transmitted from said ultrasonic oscillation mechanism 12 into a vertical-torsional composite vibration are disposed in the vicinity of the end portion of the ultrasonic horn 13.

These plurality of groove portions 1 carved in parallel with a predetermined interval respectively, have a predetermined deflection angle α with the central axis of the ultrasonic horn 13 on the circumferential surface, and this deflection angle α is set in a range of 0 degree<α<90 degrees.

Besides, the shape of the groove portion 1 is rectangular, and the width thereof is set to a range of 0.5 to 5 mm, the length 3 to 30 mm and the depth 0.5 mm or more.

In this embodiment, the ultrasonic horn 13 is formed, with titanium alloy, and the groove portion 1 is formed as shown in FIG. 17, in a vicinity of the loop position of the torsional vibration; however, the length of a tip itself is decided, specifically by the longitudinal vibration speed (vertical wave speed) $C_l$ and the torsional vibration speed (transversal wave speed) $C_t$. Consequently, the longitudinal vibration speed (vertical wave speed) $C_l$ is determined as follows by a predetermined expression, based on vertical elastic coefficient E (E=6070 m/s), transversal elastic coefficient G (G=3125 m/s) and density P (P=4.50×10$^3$ kg/m$^3$), properties of the titanium alloy:

$$C_l = 4.9 \text{ m/s}$$

Consequently, for a bar of titanium alloy, the longitudinal vibration is transmitted with a rate of 4.9 m per second, it takes 1 sec to go and back a bar of 2.45 m long.

Therefore, a length of 2.45 M is required for vibrating the titanium alloy by 1 Hz. As it is oscillated by 25 KHz in the example, in this case, the length of the bar can be determined as follows:

$$4.9 \div (2 \times 25000) = 0.000098 \text{ m}$$

Therefore, the length of the bar results in 98 mm.

Thus, the horn length corresponding to a predetermined longitudinal vibration can be determined.

Further description shall be given by FIG. 20. As shown, in the example, a restriction portion 13a is formed on the ultrasonic horn 13, and this restriction portion 13a converges the longitudinal vibration transmitted in the axial direction and allows increasing the apparent speed.

Hence, as shown in FIG. 20, in case of dividing the longitudinal vibration at the joint, the vibration becomes longer at the tip side in the ultrasonic horn 13.

Therefore, it becomes possible to set the length of the ultrasonic horn 13 variously, by changing the speed through the shape of the ultrasonic horn 13.

Similarly, it is possible to specify concretely the length of the loop position and the horn tip in the ultrasonic horn 13, in other words, the loop position where the groove portion 1 shout be set, by the torsional vibration speed. The example is designed based on the relation between respective vibration waveform and ultrasonic horn as shown in FIG. 21.

In short, the loop position is set in the ultrasonic horn 13 so that the torsional vibration be a length appropriate for the longitudinal vibration frequency (25 KHz) and the other required performance, and under this condition, the total length of the ultrasonic horn 13 is designed so that the longitudinal vibration be furthermore appropriate for the predetermined 25 KHz, and at the same time, the ultrasonic horn 13 according to the other necessity, and at this time, the position of the joint F or the longitudinal vibration component has the same effect if it is set to the left of a loop position H of the torsional vibration component as illustrated, or to the right of the loop position H.

Next, the torsional vibration attenuation means of said embodiment shall be described. In the invention of the present Application, a torsional vibration attenuation means is set between the groove portion and the ultrasonic oscillation mechanism for preventing heat generation from the vibrator, deterioration of the electrostrictive element or others, by attenuating the torsional vibration to be transmitted to the vibrator side, and in this embodiment, a circumferential surface portion having a diameter larger than the circumferential portion where the groove portion is formed on the ultrasonic horn 13 is disposed in the ultrasonic oscillation mechanism of the ultrasonic horn, to compose thereby a torsional vibration attenuation means.

In short, in FIG. 22, 13b is a torsional vibration attenuation means formed at the vibrator side of the rear end of the ultrasonic horn 13, composed of a large diameter portion 14 at the rear end portion of the ultrasonic horn 13, and an ultrasonic oscillation mechanism 12 having the same diameter as the same.

In respect to the diameter a of the circumferential surface to be set of the groove portion 1, the diameter of said large diameter portion 14 and the ultrasonic oscillation mechanism 12 joined with the same is b which is larger than a, and the torsional vibration generated by the groove portion 1 leads to said large diameter portion 14 and ultrasonic oscillation mechanism 12, and results in being diffused and attenuated.

Also, in the invention of the present Application, the torsional vibration attenuation means may be composed of a buffer having a portion area larger than the portion area in the groove portion (vertical portion in respect to the axial direction) and FIG. 23 is a diagram showing 1 embodiment of an ultrasonic hand piece having such buffer. In the drawing, 41 is a buffer provided between an ultrasonic horn 13 having a groove portion 1 and an ultrasonic oscillation mechanism 12. The portion area (vertical portion in respect to the axial direction) of this buffer 41 is formed larger than the one in the groove portion 1 and, thereby, the reciprocating rotation vibration (torsional vibration) transmitted to the ultrasonic oscillation mechanism 12 side is attenuated, allowing to prevent heat generation from the vibrator, deterioration of the electrostrictive element (PZT) or others.

The attenuation effect by the buffer can be explained as follows using FIG. 24. In the upper stage of the drawing, a horn 13 of $S_2$ and a buffer 41 connected to the rear end thereof and having a portion area $S_1$ are shown, and corresponding to this, in the lower stage of the drawing, a graphic showing the variation of displacement quantity due to the vibration is shown. It should be appreciated that $I_1$, $I_2$ show respectively the length of the buffer 41 and the horn 13.

In general, the motion equation of displacement is expressed as follows:

$$u''(x)+S'(x)u'(x)/S(x)+w^2u(x)/c^2=0$$

In the drawing, as $S_1:S_2=2:1$, the motion equation of displacement for a distance x in the longwise direction becomes as follows:

In case where the distance x is $0 \leq x \leq I_1$, $u = u_0 \cos \mu x$

In case where the distance x is $I_1 \leq x \leq I_2$, $u = u_0 (S_1/S_2)^2 \cos \mu x$ Here, $u_0$ represent the displacement in case of x=0, while $\mu = 2\pi f/c$, c represent the acoustic velocity.

According to the foregoing, if the displacement at x=0 and $I_2$ is determined, $u_0=1$, $u_{12}=4$ are obtained. In short, for the vibration toward the horn tip, namely when x varies from 0 to $I_2$, the displacement is multiplied by 4, and on the contrary, for the return vibration, namely when x varies from $I_2$ to 0, the displacement is divided by 4.

As mentioned hereinbefore, the return vibration from the horn toward the vibrator can be attenuated by providing an attenuation portion of the aforementioned condition, between the horn 13 and the vibrator.

In the invention of the present Application, the following effects can be expected, by the configurative function described hereinbefore.

(1) At the working portion of the tip of an ultrasonic horn, as a composite vibration of vertical-torsional vibration is output at the working portion of the tip of the ultrasonic horn, the sharpness in motion increases, subtle motions become easier, the operability in surgical operation or processing of various materials increases remarkably, and the work efficiency also increases.

(2) As a desired composite vibration of vertical-torsional vibration can be obtained only with a longitudinal vibration element, miscellaneous costs including the manufacturing cost can be reduced, maintenance and custody are easy, and the durability is excellent. As a composite vibration of vertical-torsional vibration is output, the sharpness in motion increases, subtle motions become easier, the operability in surgical operation or processing of various materials increases remarkably, and the work efficiency also increases.

(3) The torsional vibration attenuation means allows to mitigate heat generation from the vibrator, deterioration of the electrostrictive element or others, provoked by the transmission of torsional vibration in respect to the ultrasonic oscillation mechanism.

(4) In the female portion, as the displacement speed of the non-working plane can be attenuated in comparison with the displacement speed of the working plane, the damage of live body tissues or others by the non-working plane can be prevented.

What is claimed is:

1. A complex vibration ultrasonic hand piece, comprising an ultrasonic oscillation mechanism composed of a longitudinal vibration element, backing plates attached to both ends thereof and a front plate for generating an ultrasonic vibration of a predetermined frequency, a horn coupled with said ultrasonic oscillation mechanism for amplifying the vibration transmitted from said ultrasonic oscillation mechanism, a vibration conversion mechanism for converting the vibration transmitted from said ultrasonic oscillation mechanism into a composite vibration composed of a longitudinal vibration in the horn central axial direction and a torsional vibration having the horn central axis as a fulcrum, and a female portion provided with a working plane and disposed at said horn tip, wherein:

said vibration conversion mechanism, between said horn tip and an electrostrictive element of said ultrasonic oscillation mechanism, is composed of one or more groove portions formed on the external surface of any of the horn, the ultrasonic oscillation mechanism or a member interposed between the horn and the ultrasonic oscillation mechanism.

2. The complex vibration ultrasonic hand piece of claim 1, wherein:

said horn is composed of a horn of ½ wavelength or more, and a speed variation mechanism of torsional vibration in said composite vibration is formed in said female portion, for reducing the reciprocating rotation speed of non working plane less than the speed of the working plane.

3. The complex vibration ultrasonic hand piece of claim 2, wherein:

said groove portions are juxtaposed in plurality, said speed variation mechanism of reciprocating rotation in the female portion is composed of a projection portion formed on a shaft side face of the female portion, and a working plane is provided at a projection portion tip plane for reducing the torsional vibration speed of the non working plane less than the speed of the working plane.

4. The complex vibration ultrasonic hand piece of claim 2, wherein:

said groove portions are juxtaposed in plurality, said speed variation mechanism of reciprocating rotation in the female portion is composed of a curved surface body having a small diameter portion and a large diameter portion formed on a tip of the female portion, and a working plane is provided on said large diameter portion for reducing the torsional vibration speed of the non working plane less than the speed of the working plane.

5. The complex vibration ultrasonic hand piece of claim 4, wherein:

said curved surface body is a sphere or a pseudo sphere.

6. The complex vibration ultrasonic hand piece of claim 4, wherein:

said curved surface body is a spindle or a pseudo spindle.

7. The complex vibration ultrasonic hand piece of claim 2, wherein:

said groove portion is formed spiral.

8. The complex vibration ultrasonic hand piece of claim 2, wherein:

said groove portion has a predetermined deflection angle $\alpha$ on a circumferential surface to the central axis of said horn and/or said ultrasonic oscillation mechanism, and said deflection angle is set to $0<\alpha<90$ degrees.

9. The coupling oscillation ultrasonic hand piece of claim 2, wherein:

the groove portion is disposed in the vicinity of the antinode position of the torsional vibration.

10. The complex vibration ultrasonic hand piece of claim 2, wherein:

a torsional vibration attenuation means is interposed between the groove portion and an electrostrictive element of the ultrasonic oscillation mechanism, and said torsional vibration attenuation means is composed of a circumferential surface portion of a diameter larger than that of the circumferential surface portion where the groove portion is formed.

11. The complex vibration ultrasonic hand piece of claim 2, wherein:

a torsional vibration attenuation means is interposed between the groove portion and an electrostrictive element of the ultrasonic oscillation mechanism, and said torsional vibration attenuation means is composed of a buffer having the area of a cross-section larger than that of the cross-section (longitudinal cross-section in respect to the axial direction) in the groove portion.

12. The complex vibration ultrasonic hand piece of claim 2, wherein:

the vibration conversion mechanism comprises a main body detachably interposed between the horn and the ultrasonic oscillation mechanism and a groove portion formed around the main body circumferential surface.

* * * * *